US005314421A

United States Patent [19]

Leuenberger

[11] Patent Number: 5,314,421

[45] Date of Patent: May 24, 1994

[54] BLOOD PACK LABELS AND THE LIKE

[75] Inventor: Mark Leuenberger, Gurnee, Ill.

[73] Assignee: Baxter International Inc., Deerfield, Ill.

[21] Appl. No.: 847,165

[22] Filed: Mar. 5, 1992

[51] Int. Cl.[5] ........................ A61B 19/00; B42D 15/00

[52] U.S. Cl. .................................... 604/403; 283/117; 283/81; 604/408

[58] Field of Search .................. 283/81; 604/189, 403, 604/404, 405, 408

[56] References Cited

U.S. PATENT DOCUMENTS

| | | | |
|---|---|---|---|
| 3,619,568 | 11/1971 | Taplin . | |
| 3,905,477 | 9/1975 | Graham | 604/189 X |
| 3,938,519 | 2/1976 | McPhee | 604/404 |
| 4,132,594 | 1/1979 | Bank et al. | 604/405 X |
| 4,198,972 | 4/1980 | Herb . | |
| 4,337,768 | 7/1982 | Hatada et al. . | |
| 4,472,357 | 9/1984 | Levy et al. . | |
| 4,496,361 | 1/1985 | Kilkson . | |
| 4,526,404 | 7/1985 | Vazquez . | |
| 4,678,458 | 7/1987 | Fredeking | 604/189 X |
| 4,880,425 | 11/1989 | Kuhlemann et al. . | |
| 4,902,287 | 2/1990 | Carmen et al. . | |
| 4,994,057 | 2/1991 | Carmen et al. . | |
| 5,100,491 | 3/1992 | Ijiri et al. . | |
| 5,125,920 | 6/1992 | Ishida | 604/408 X |
| 5,132,026 | 7/1992 | Baloyot et al. | 604/405 X |

OTHER PUBLICATIONS

Teslin.

Inventions That Have Made Extraordinary Lasting Impressions Fire Polyart 2-.

The Synthetic That's Virtually As Easy to Print as Paper Polyart2-.

Properties, Printing & Conversion.

Polyart 2-The Synthetic Paper.

*Primary Examiner*—Paul A. Bell

*Attorney, Agent, or Firm*—Bradford R. L. Price; Paul C. Flattery; Robert M. Barrett

[57] ABSTRACT

A label for a blood pack comprising a microporous plastic film including a matrix of interconnected pores for allowing gas to flow into and out of the blood pack through a labeled area. The pores allow ink to be absorbed at least on an outer surface of the label allowing the label to be printed and/or written on. The labels of the present invention have breathability with respect to gas that is similar to paper. However, the label is more durable than a paper label in that it can tolerate moisture, abrasion, temperature extremes, dimensional changes, and the like. Accordingly, the labels do not crack or wrinkle as easily as paper labels.

4 Claims, 5 Drawing Sheets

BLOOD PACK LABELS AND THE LIKE

BACKGROUND OF THE INVENTION

The present invention relates to blood packs generally. More specifically, the present invention relates to labels for blood packs.

It is known to house blood components in flexible plastic containers. These containers referred to as either blood packs or blood bags can be used to receive a blood component, process the blood component, store the blood component, and assist in infusing the blood component into a recipient. Of course, it is necessary to provide some means for identifying certain information on the blood pack, e.g., the type of storage solution, anticoagulant, or blood component, the collection date, manufacturer's product code and lot number, etc.

To this end, it is known to provide labels for blood packs. Typically, these labels have heretofore comprised a paper substrate that is secured to the container. These paper labels provide many characteristics that are necessary and/or desirable for a blood pack label.

Blood packs must provide a container that allows gas transmission through the container in order to maintain the viability of the cells to be housed therein. In this regard, it is necessary that the bag allow carbon dioxide to flow out of the blood pack and oxygen to flow therein. Paper provides a substrate that allows for a flow of gas through the labeled area of the blood pack; a paper label does not decrease the effective area of the bag that allows gas transmission beyond acceptable limits.

Paper also provides a surface that can be written or printed on. Thus, a paper label provides a substrate that allows one to easily indicate necessary information on the blood pack. In this regard, the label typically will receive printed as well as handwritten information. It is also known to use bar codes on such labels.

Paper, however, does exhibit certain disadvantages when used as a label for a blood pack. Paper labels are not very durable to moisture, abrasion, temperature extreme, and are not elastic to allow for dimensional changes that occur to the blood pack. It is known to process the blood components stored within the blood packs by centrifuging the bag in addition to other processes. During such processes the labels can become wet and subjected to extreme temperatures. Paper labels can crack or wrinkle during such processes. The cracking or wrinkling of a label is especially detrimental to the use of bar codes on such labels. Unless a smooth uninterrupted surface is provided, the bar codes may be unreadable by a bar code reader. This forces manual entering of data into a computer thus increasing the chance for errors.

There are a number of other requirements that a blood pack label must meet. Some such requirements are set forth in the labeling requirements that have been instituted by the: American Blood Commission's Uniform Labeling Guidelines 1985; or NBTS "Spec for Uniform Labeling of Blood and Blood Products."

It is also desirable that blood pack labels be easily applied to the blood pack. Such labels must also endure the typical manufacturing processing conditions that are typically utilized. In this regard, the bag and label must be sterilizable. Further, the labels must be able to withstand the processing conditions that the containers may be subjected to by the customer, for example, centrifugation, liquid freezing, water bath thawing to name a few.

SUMMARY OF THE INVENTION

The present invention provides a label for a blood pack that provides the desirable characteristics of a paper label but not the disadvantages. The labels of the present invention have a permeability with respect to gas that is similar to paper. Additionally, the label will accept printing as easily as paper. However, the label is more durable than a paper label in that it can tolerate moisture, abrasion, temperature extremes, dimensional changes, and the like. Accordingly, the labels do not crack or wrinkle as easily as paper labels.

The present invention provides a label for a blood pack comprising a microporous plastic film including a matrix of interconnected pores for allowing gas to flow into and out of the blood pack through a labeled area. The pores allow ink to be absorbed at least on an outer surface of the label allowing the label to be printed and/or written on.

In an embodiment, the label includes either a pressure or heat sensitive adhesive on a bottom surface thereof for allowing the label to be secured to the blood pack.

In an ambodiment, the label includes one or more bar codes printed thereon.

The present invention also provides a blood pack that includes a label that is constructed from a microporous plastic film including a matrix of interconnected pores for allowing gas to flow into and out of the blood pack through a labeled area. At least the pores located on an outer surface of the label are so constructed and arranged to receive ink allowing the label to be written on.

In an embodiment, the label is secured to the blood pack by a pressure or heat sensitive adhesive.

The present invention also provides a method for labeling a blood pack comprising the steps of: applying a label comprising microporous plastic film to the blood pack; allowing gas to flow through pores in the label into and out of the blood bag; and writing on the label by causing ink to be received within pores located on an outer surface of the label.

An advantage of the present invention is that the microporous surface of the label also allows other labels to be applied to the original bag labels such that their adhesives utilize the porous surface of the first label to form permanent bonds.

Another advantage of plastic labels of the present invention is that the label does not contain some of the typical undesirable chemical constituents of paper, such as formaldehyde.

Additional features and advantages of the present invention are described in, and will be apparent from, the detailed description of the presently preferred embodiments and from the drawings.

BRIEF DESCRIPTION OF THE DRAWINGS

FIG. 3b is a photomicrograph of a magnification (300 times) of the labeling surface of the paper prior art label of FIG. 3a.

FIG. 4b is a magnification (300 times) of the labeling surface of the embodiment of the label of FIG. 4a.

DETAILED DESCRIPTION OF THE PRESENTLY PREFERRED EMBODIMENTS

The present invention provides an improved label for blood packs and the like. The label exhibits the desirable properties of paper labels, but does not also exhibit a number of disadvantages associated with paper, such as lack of durability.

The labels of the present invention provide gas transmission, permeability through the label, into and out of the blood pack, similar to a paper label. Further, the labels are as easily printed on, either by writing or a printing process, as a paper label. However, the labels of the present invention are more durable with respect to moisture, abrasion, temperature extremes, and dimensional changes than are paper labels. Accordingly, the labels do not crack and wrinkle as easily as paper labels.

The labels of the present invention comprise a microporous plastic film. The microporous plastic film is constructed by processing methods that cause the material to consist of a matrix of interconnected microsize pores that allow gases and vapors to flow freely therethrough. A number of processes can be used to create such a film including, but not limited to, stretching the film, radiation treatment of the film, and addition of film additives such as fillers that may or may not be removed from the film during processing.

Figure 1:
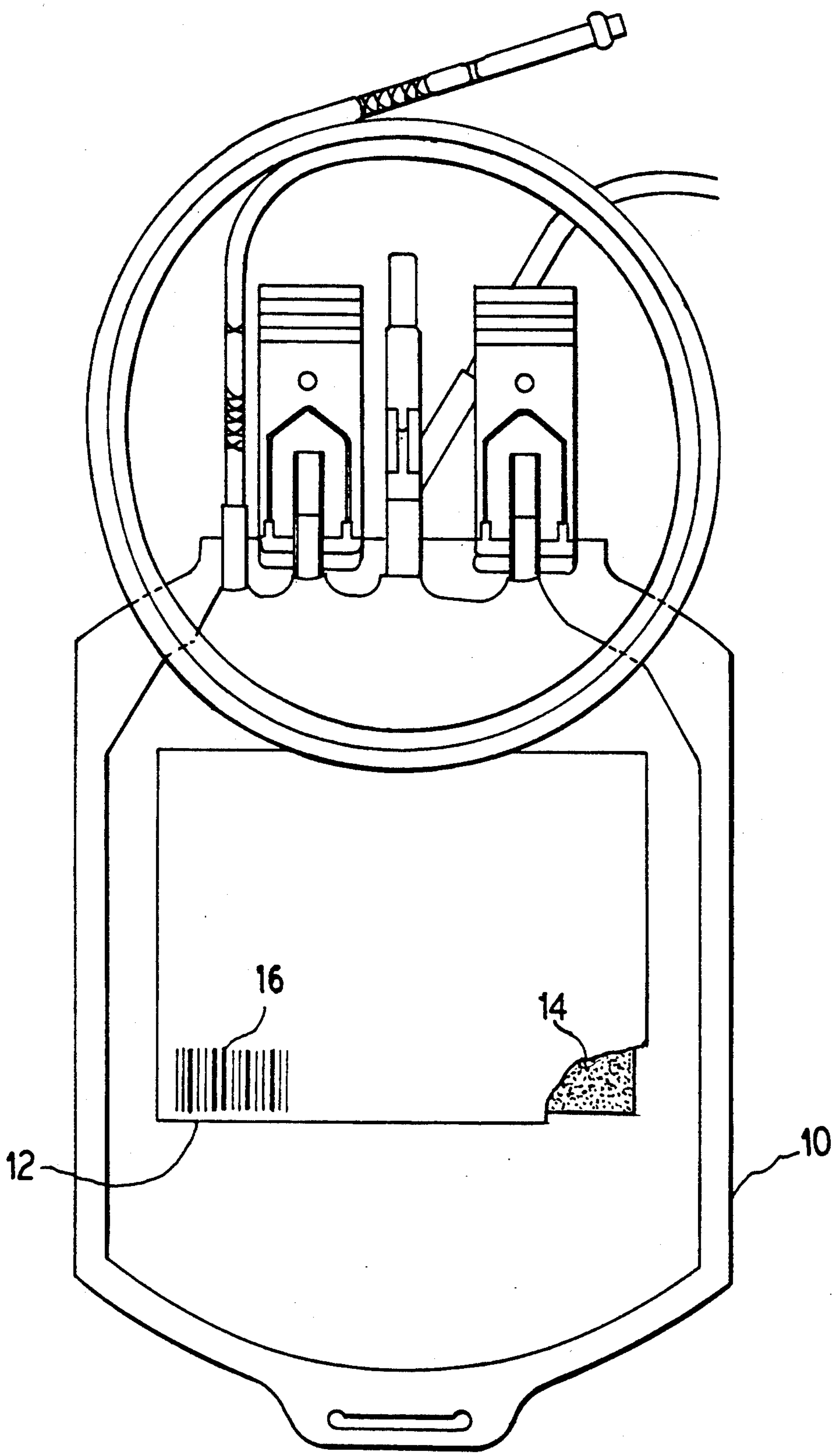
FIG. 1 illustrates a blood pack including the label of the present invention.
Figure 2A:
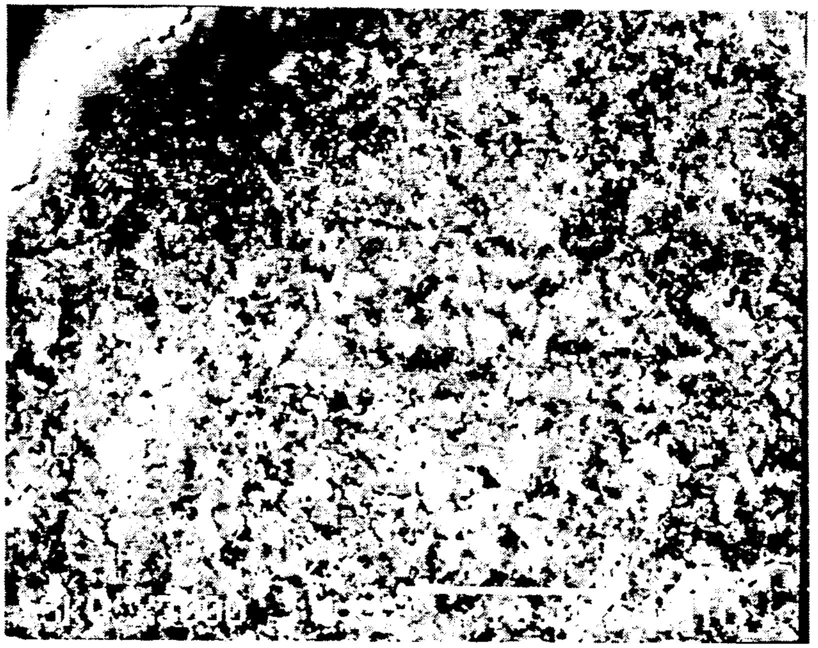
FIG. 2*a* is a photomicrograph of a surface magnification (3,000 times) of the labeling surface of a current prior art paper label.
Figure 2B:
FIG. 2*b* is a photomicrograph of a surface magnification (3,000 times) of the labeling surface of an embodiment of a label of the present invention.
Figure 3A:
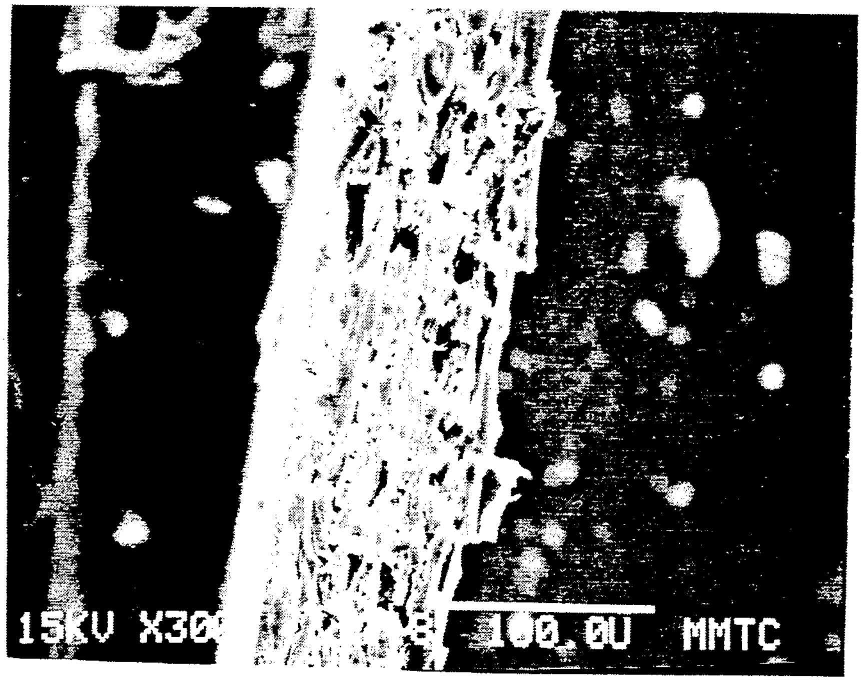
FIG. 3a is a photomicrograph of a cross-sectional magnification (300 times) view of a current prior art paper label including an adhesive layer.
Figure 3B:
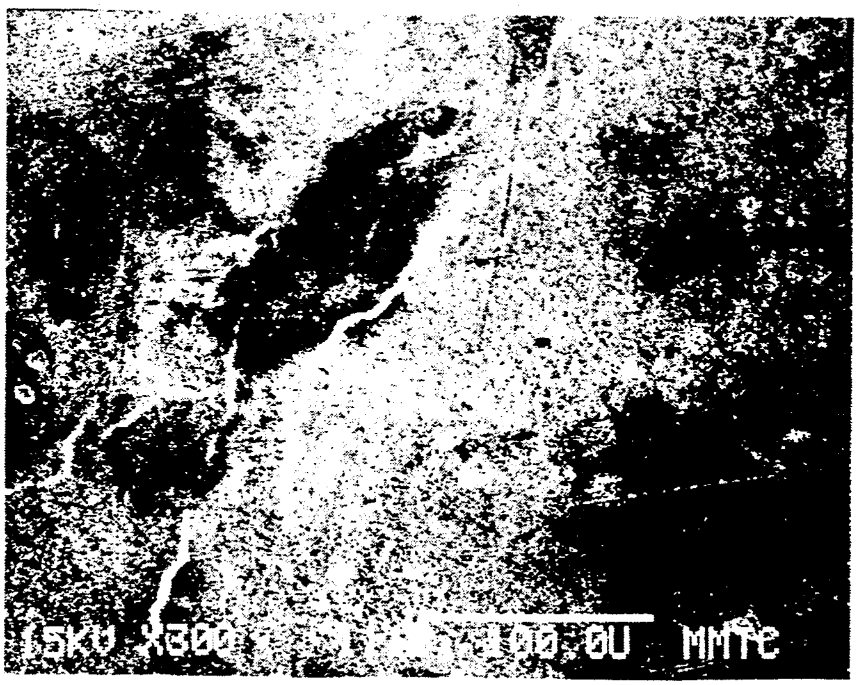
Figure 4A:
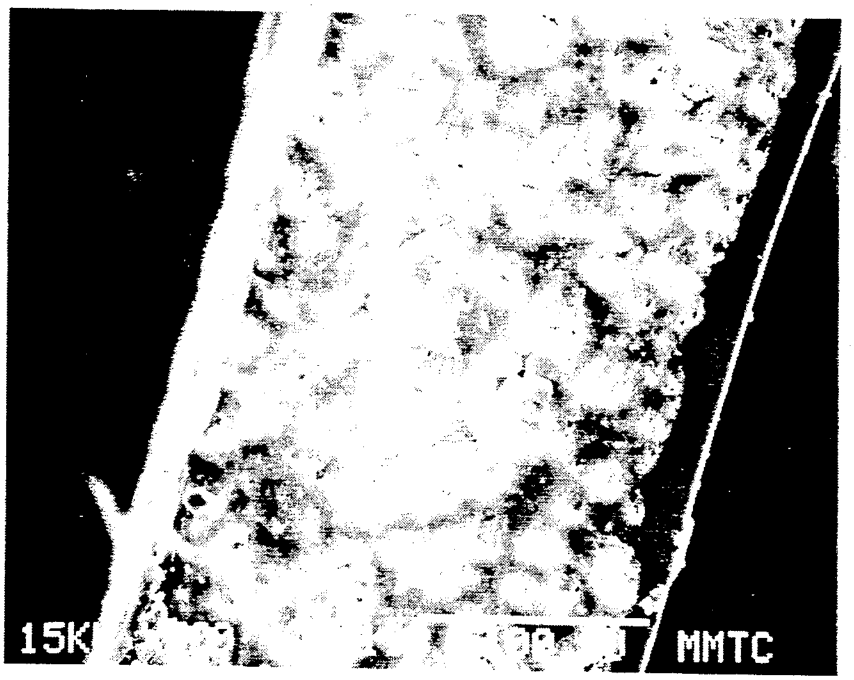
FIG. 4a is a photomicrograph of a cross-sectional magnification (300 times) view of an embodiment of a label including an adhesive layer of the present invention.
Figure 4B:
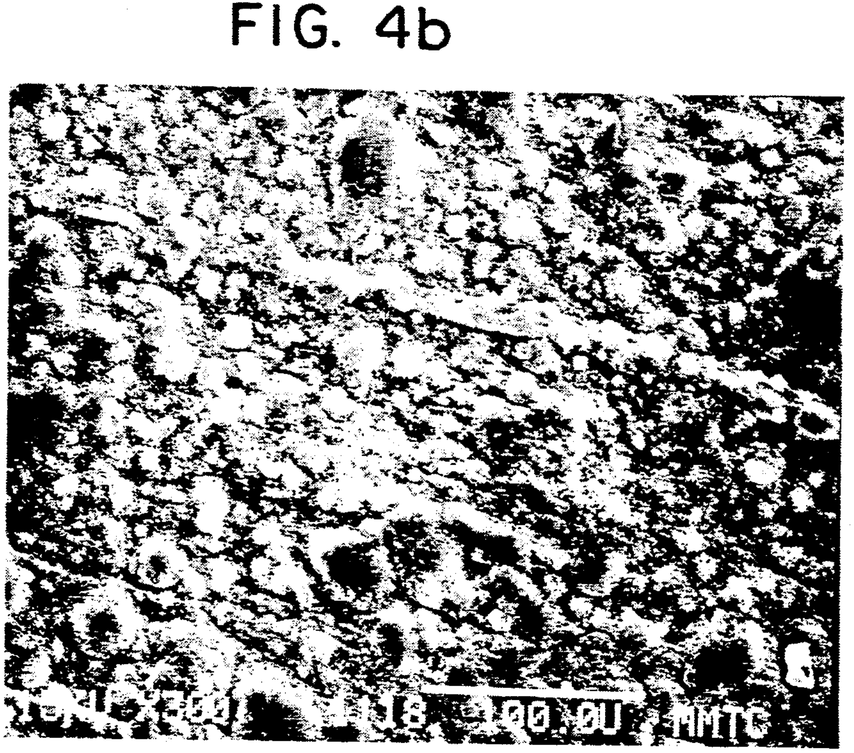
Figure 5:
FIG. 5 is a surface magnification (10,000 times) at higher magnification of an embodiment of the label of the present invention.

Referring now to FIG. 1, a blood pack 10 including the blood label 12 of the present invention is illustrated. As illustrated, the blood pack 10 defines a container for receiving and storing a blood component. The blood pack 10 is constructed from a plastic material, such as plasticized polyvinyl chloride. Such blood packs are available from Baxter Healthcare Corporation, Fenwal Division, Deerfield, Ill..

The label 12 is secured to the blood pack 10 to allow one to identify the blood pack. To this end, as illustrated, the label can be printed on, as well as include a bar code 16. It is also common practice to write on the label. The label 12 of the present invention allows one to easily identify the blood pack for inventory purposes, to determine what is in the blood pack, expiration date, and the like.

The label 12 includes interconnected microsize pores that allow gases and vapors to flow freely through the blood pack 10 and label 12. In this regard, carbon dioxide generated within the container will flow out of the blood pack 10 and oxygen necessary for the cell's viability will flow into the blood pack. The size of the pores and/or controlled coatings between the adhesive layer and back side of the label can be varied to control the rate of gas exchange. As set forth in detail below, the labels 12 of the present invention provide sufficient gas permeability.

It has been found that the microporous label of the present invention meets the necessary and desirable requirements for a blood pack label. These requirements include being non-removable, in an intact state, from the pack, or not reappliable, tamper evident, to another bag once removed by the customer.

Due to the microporous structure of the label, the label can easily be written on or printed on. To this end, the pores near the outer surface of the label will receive ink and therefore allow the label to be written on or printed on, such as with a bar code. In this regard, the label will accept writing or ink stamping on its surface and will not smear five seconds after being printed on with a variety of means.

The label when scanned with a bar code reader will read accurately. An advantage of the label of the present invention over a paper label is that the label will not wrinkle or crack during processing conditions and accordingly, can be bar code read accurately by a standard bar code reader multiple times without deterioration of read rates.

The label is visually acceptable from an aesthetic standpoint and is not adversely effected by manufacturing and processing conditions, i.e., it will not wrinkle, crack, split, scuff, fade, etc., during processing conditions.

The label additionally complies with the American Blood Commission's "Uniform Labelling Guidelines" (1985 & Draft 1989).

The labels of the present invention can also be applied using currently available labeling equipment and methods with minimal modification. To this end, the label can either include a pressure or heat sensitive adhesive 14 to be sealed to the blood pack.

The label is not adversely affected by processing conditions of manufacturing. These processing conditions include sterilization, such as: steam sterilization in plastic overwraps; steam pasteurization, in foil pouch; ozone pasteurization; Eto sterilization; and Gamma or EBeam sterilization.

The labels of the present invention are not adversely affected by warehouse/shipping conditions during useful shelf life of finished product (i.e., 30-36 months) or raw label materials before application (i.e., 2 years).

An example of a microporous label material that can be used in the present invention includes Teslin, a microporous polyolefin film manufactured by PPG Industries.

BAG AND LABEL MATERIAL GAS PERMEABILITY
UNITS = (CC/100 $IN^2$/24 HOURS)*

| | Container #1 Plasticized PVC | | Container #2 Plasticized PVC | | Container #3 Polyolefin | | Container #4 Plasticized PVC | |
|---|---|---|---|---|---|---|---|---|
| | $O_2$* | $CO_2$* | $O_2$* | $CO_2$* | $O_2$* | $CO_2$* | $O_2$* | $CO_2$* |
| LABEL MATERIALS (below) | | | | | | | | |

-continued

| BAG AND LABEL MATERIAL GAS PERMEABILITY UNITS = (CC/100 $IN^2$/24 HOURS)* | | | | | | | | |
|---|---|---|---|---|---|---|---|---|
| | Container #1 Plasticized PVC | | Container #2 Plasticized PVC | | Container #3 Polyolefin | | Container #4 Plasticized PVC | |
| | $O_2$* | $CO_2$* | $O_2$* | $CO_2$* | $O_2$* | $CO_2$* | $O_2$* | $CO_2$* |
| Paper Labels | | | | | | | | |
| 1 | 23 | 132 | 18 | 186 | — | — | 34 | 537 |
| 2 | — | — | — | — | 91 | 426 | — | — |
| 3 | — | — | — | — | 123 | 616 | — | — |
| Microporous Labels | | | | | | | | |
| 4 | 27 | 220 | 54 | 703 | — | — | 56 | 506 |
| 5 | 24 | 204 | 59 | 285 | 222 | 667 | 52 | 383 |
| 6 | 26 | 209 | 49 | 285 | 101 | 682 | 72 | 660 |
| 7 | 27 | 185 | 56 | 318 | 114 | 765 | 60 | 572 |

Tested per ASTM #03985 for $O_2$
Through Label Material and Bag Material Combined
(Modified for $CO_2$ by Using Infrared Detector)

1. Paper Label available from DRG, Madison, Wis. under the designation Newton Falls paper with heat activated adhesive. 2. Paper label available from Modern Press, Sioux Falls, S. Dak., under the designation Champion Kromekote paper with pressure sensitive adhesive. 3. Paper label available from Modern Press, Sioux Falls, S. Dak., under the designation Champion Kromekote paper with pressure sensitive adhesive. 4. Microporous Film Label from 3M with pressure sensitive adhesive. 5. Microporous Film Label from 3M with pressure sensitive adhesive. 6. Microporous Film Label from Avery Label, Azusa, Calif. with pressure sensitive adhesive. 7. Microporous Film Label from Avery Label, Azusa, Calif. with pressure sensitive adhesive.

Referring now to FIGS. 2-5, electron microscopy photographs at different magnifications for currently used paper labels and labels of the present invention are illustrated. The label of the present invention illustrated in the photos (FIGS. 2*b*, 4*a*, 4*b*, and 5) are made with Teslin from PPG Industries. The microphotographs are consistent with the test results set forth above demonstrating porosity at least as good as the porosity of paper labels.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A blood pack including a label wherein the label including a substrate having a top surface capable of receiving ink and a bottom surface providing means for securing the label to a blood pack, the substrate being constructed from a microporous plastic film including a matrix of interconnected pores for allowing gas to flow into and out of the blood pack through the label, at least pores located on an outer surface of the label being so constructed and arranged to receive ink allowing the label to be written on, the blood pack being defined by plastic sheets that are sealed along edges thereof to define an interior for receiving and storing blood.

2. The blood pack of claim 1 wherein the label is secured to the blood pack by a pressure sensitive material.

3. The blood pack of claim 1 wherein the label is heat sealed to the blood pack.

4. The blood pack of claim 1 wherein the label includes a bar code printed thereon.

* * * * *